(12) United States Patent
Siccardi et al.

(10) Patent No.: US 10,350,087 B2
(45) Date of Patent: Jul. 16, 2019

(54) SET OF INSTRUMENTS FOR THE IMPLANTATION OF AN ACETABULAR PROSTHESIS

(71) Applicant: MEDACTA INTERNATIONAL SA, Castel San Pietro (CH)

(72) Inventors: Alberto Siccardi, Sonvico (CH); Francesco Siccardi, Vico Morcote (CH); Massimiliano Bernardoni, Figino (CH); Matteo Ponzoni, Montano Lucino (IT)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 0 days.

(21) Appl. No.: 15/809,171

(22) Filed: Nov. 10, 2017

(65) Prior Publication Data
US 2018/0085231 A1    Mar. 29, 2018

Related U.S. Application Data

(62) Division of application No. 14/777,717, filed as application No. PCT/IB2014/059715 on Mar. 13, 2014, now abandoned.

(30) Foreign Application Priority Data

Mar. 18, 2013  (IT) .............................. MI2013A0405

(51) Int. Cl.
*A61B 17/00* (2006.01)
*A61F 2/46* (2006.01)
(Continued)

(52) U.S. Cl.
CPC ............ *A61F 2/4609* (2013.01); *A61B 17/16* (2013.01); *A61B 17/1666* (2013.01);
(Continued)

(58) Field of Classification Search
None
See application file for complete search history.

(56) References Cited

U.S. PATENT DOCUMENTS

| | | |
|---|---|---|
| 5,100,407 A | 3/1992 | Conrad et al. |
| 5,112,336 A | 5/1992 | Krevolin et al. |

(Continued)

FOREIGN PATENT DOCUMENTS

| | | |
|---|---|---|
| EP | 1561438 | 8/2005 |
| EP | 2491873 | 8/2012 |

(Continued)

*Primary Examiner* — Sameh R Boles
(74) *Attorney, Agent, or Firm* — Allen, Dyer, Doppelt, + Gilchrist, P.A.

(57) ABSTRACT

A method is for implantation of an acetabular prosthesis. The method may include positioning an acetabular calibration guide at an acetabular cavity of a patient, and positioning an acetabular reference guide at a bone site of the patient separate from the acetabular cavity. The method may include aligning a calibration signal and a reference signal, the calibration and reference signals being respectively associated with the acetabular calibration guide and the acetabular reference guide. The method may include removing the acetabular calibration guide and positioning a tool at the acetabular cavity of the patient, and aligning a control signal and the reference signal for identifying a desired orientation of the tool relative to the acetabular cavity, the control signal being associated with the tool.

18 Claims, 18 Drawing Sheets

(51) Int. Cl.
    *A61B 17/16*            (2006.01)
    *A61B 17/17*            (2006.01)
    *A61B 17/92*            (2006.01)
    *A61F 2/34*             (2006.01)
    *A61F 2/30*             (2006.01)
    *A61B 17/56*            (2006.01)

(52) U.S. Cl.
    CPC .......... *A61B 17/1746* (2013.01); *A61B 17/92* (2013.01); *A61F 2/34* (2013.01); *A61F 2/4657* (2013.01); *A61B 2017/00725* (2013.01); *A61B 2017/568* (2013.01); *A61F 2002/3097* (2013.01); *A61F 2002/4687* (2013.01)

(56) References Cited

U.S. PATENT DOCUMENTS

| | | | |
|---|---|---|---|
| 5,141,512 A | 8/1992 | Farmer et al. | |
| 5,258,032 A | 11/1993 | Bertin | |
| 5,578,037 A | 11/1996 | Sanders et al. | |
| 5,601,563 A | 2/1997 | Burke et al. | |
| 5,683,397 A | 11/1997 | Vendrely et al. | |
| 5,702,460 A | 12/1997 | Carls et al. | |
| 5,919,195 A | 7/1999 | Wilson et al. | |
| 6,117,138 A | 9/2000 | Burrows et al. | |
| 6,302,890 B1 | 10/2001 | Leone, Jr. | |
| 6,395,004 B1 | 5/2002 | Dye et al. | |
| 6,558,391 B2 | 5/2003 | Axelson, Jr. et al. | |
| 6,695,850 B2 | 2/2004 | Diaz | |
| 6,712,823 B2 | 3/2004 | Grusin et al. | |
| 7,011,664 B2 | 3/2006 | Haney et al. | |
| 7,074,224 B2 | 7/2006 | Daniels et al. | |
| 7,241,298 B2 | 7/2007 | Nemec et al. | |
| 7,601,155 B2 | 10/2009 | Petersen | |
| 7,794,467 B2 | 9/2010 | McGinley et al. | |
| 7,828,806 B2 | 11/2010 | Graf et al. | |
| 8,007,448 B2 | 8/2011 | de La Barrera | |
| 8,206,405 B2 | 6/2012 | Beverland et al. | |
| 9,161,844 B2 * | 10/2015 | Taylor | A61F 2/34 |
| 9,339,278 B2 | 5/2016 | Meridew et al. | |
| 2004/0073225 A1 | 4/2004 | Subba Rao | |
| 2005/0177172 A1 | 8/2005 | Acker et al. | |
| 2006/0122616 A1 | 6/2006 | Bennett et al. | |
| 2008/0208200 A1 | 8/2008 | Crofford | |
| 2011/0190775 A1 | 8/2011 | Ure | |
| 2012/0109137 A1 | 5/2012 | Iannotti et al. | |
| 2013/0046310 A1 | 2/2013 | Ranawat et al. | |

FOREIGN PATENT DOCUMENTS

| | | |
|---|---|---|
| JP | 2003260064 | 9/2003 |
| WO | WO 2011117644 | 9/2011 |

* cited by examiner

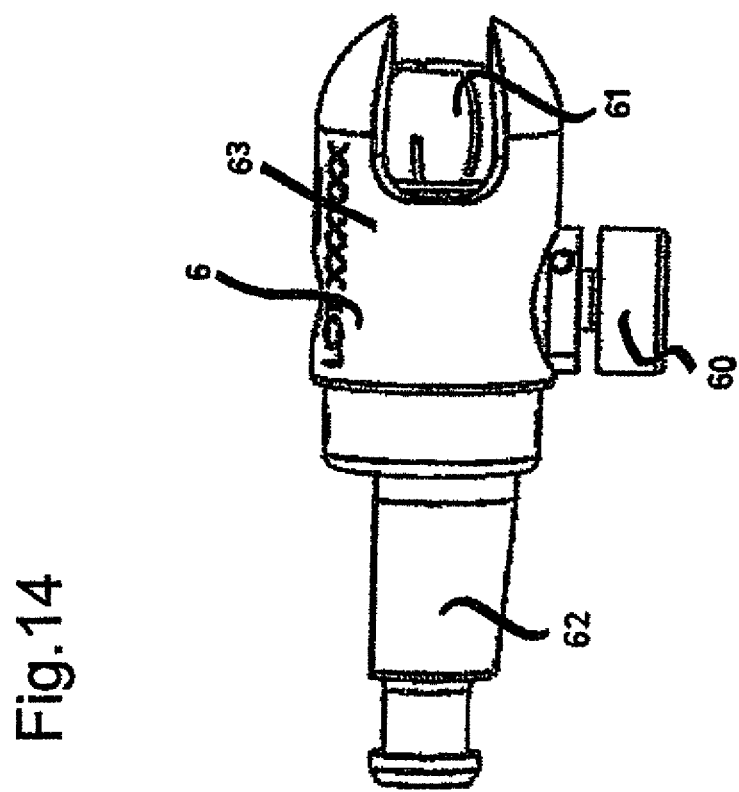
Fig.14
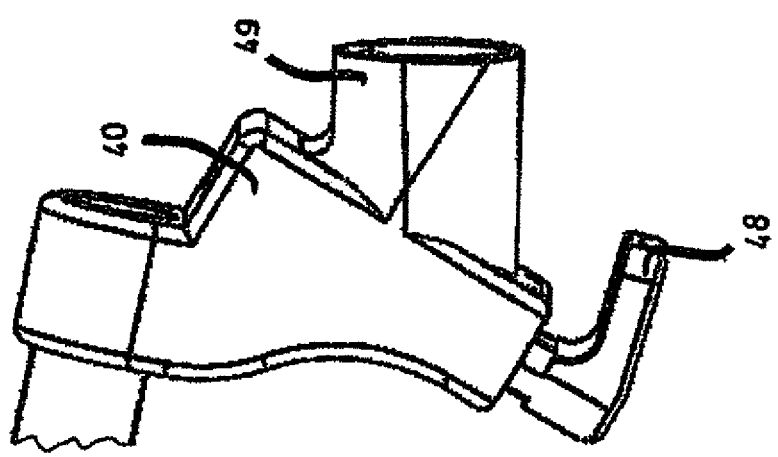

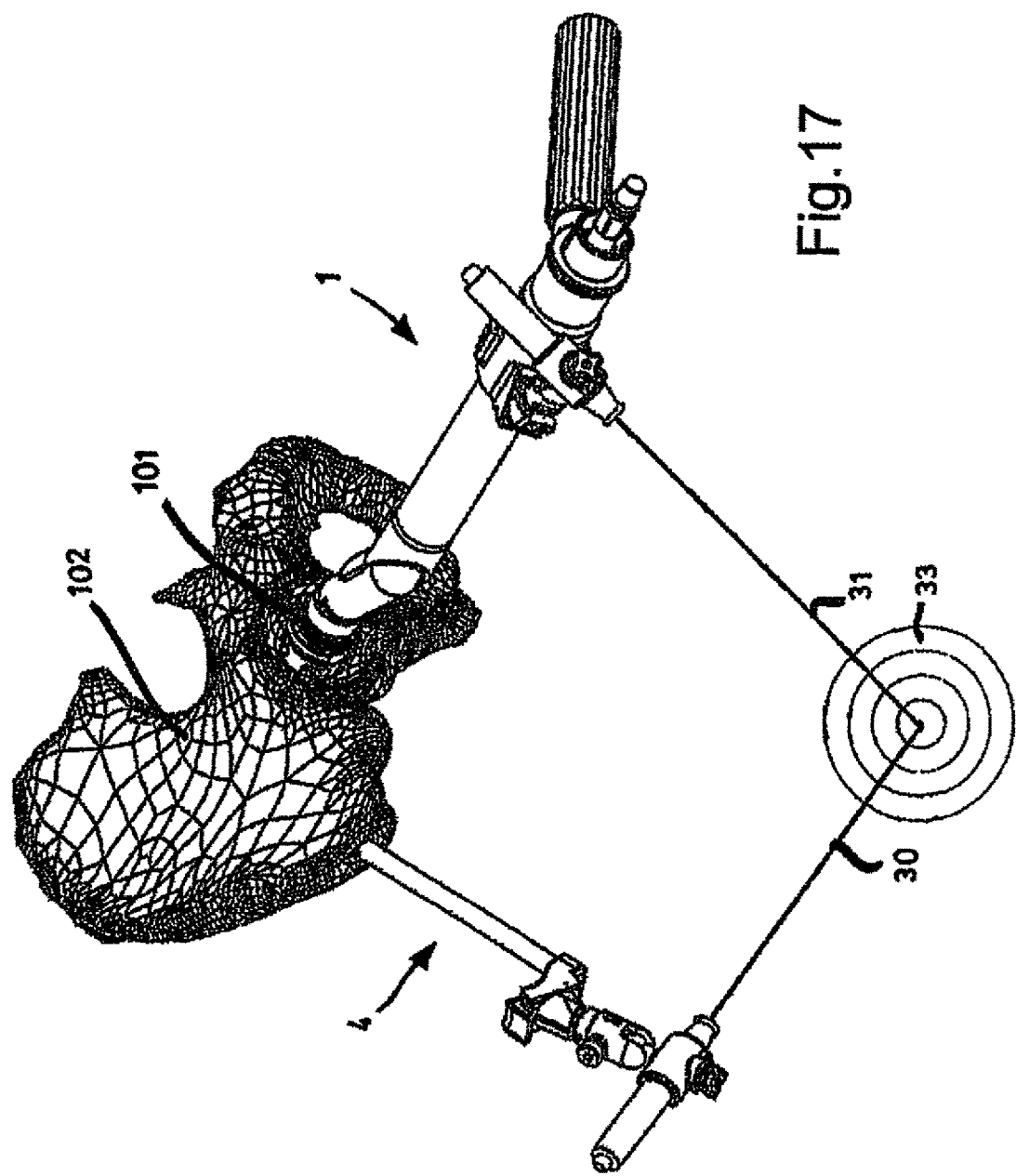

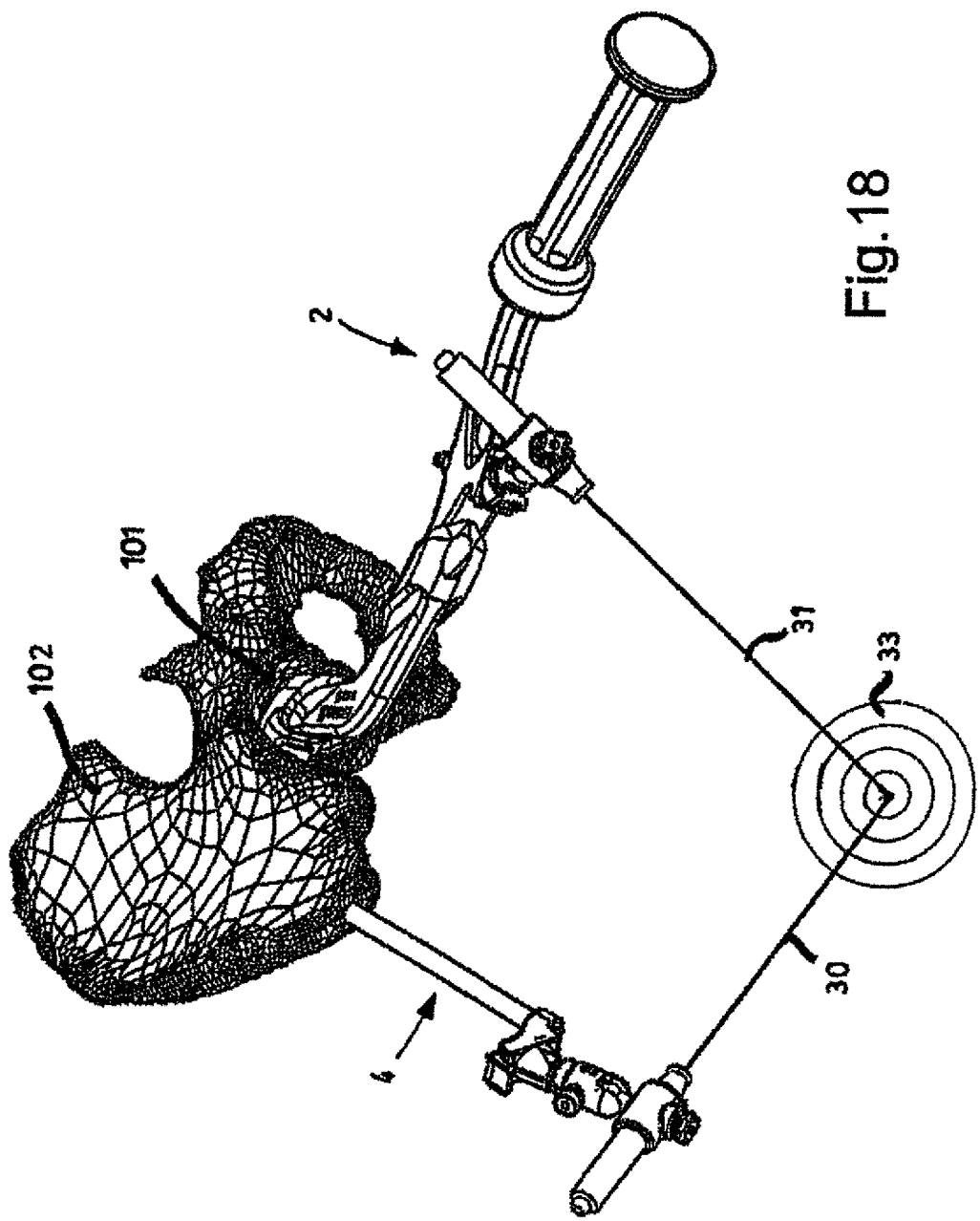

SET OF INSTRUMENTS FOR THE IMPLANTATION OF AN ACETABULAR PROSTHESIS

RELATED APPLICATIONS

This application is a divisional of U.S. application Ser. No. 14/777,717 filed Sep. 16, 2015, which is a 371 of International application No. PCT/IB2014/059715 filed Mar. 13, 2014, which claims priority to Italian Application No. MI2013A000405 filed Mar. 18, 2013, each application is hereby incorporated herein in its entirety by reference.

FIELD OF THE INVENTION

The present invention relates to a medical device, and more particularly to, a set of instruments for the implantation of an acetabular prosthesis.

BACKGROUND

The use of endoprostheses to eliminate pain and restore the function of the hip joint, especially in patients suffering from osteoarthritis, is a technique that was developed starting from the second half of the last century and is by now well established in the medical art. In most cases, where both the acetabular cavity and the femoral head of the patient are compromised by the pathology, a total arthroprosthesis of the hip, also called THR—acronym for total hip replacement—is performed. This operating technique entails the implantation of an acetabular prosthesis in the patient's pelvis on the one hand and, on the other hand, the resection of the femoral head and replacement thereof with a prosthetic stem endowed with an articulating ball that fits into the aforesaid prosthesis.

Despite having led to some excellent clinical results in terms of functional recovery of the joint, arthroprosthesis of the hip has some major drawbacks. In particular, it has been observed, due to the reduced diameter of the prosthetic ball, there are frequent episodes of displacement of the artificial joint; not rarely, for the same reason, an arthroprosthesis performed without the necessary precision and expertise may lead to a disparity in the length of the lower limbs. Finally, arthroprosthesis of the hip does not enable the patient to engage in sports or other stressful activities, making this an unsuitable solution especially for younger patients.

In order to remedy the drawbacks observed in the art, an alternative to the traditional arthroprosthesis of the hip has been developed in recent times, namely, hip resurfacing. This approach involves capping the articular surface of the pelvis and femoral head with metal cups of modest thickness, thereby preserving both the head and neck of the patient's femur. This operation makes it possible to maintain a joint diameter that is close to the physiological one, thus reducing the risk of displacements and modifications in the length of the limb. Furthermore, the wear on the components is more limited, with a consequent lengthening in the average lifespan of the prosthesis.

Both operating approaches summarily described here have in common the need to prepare the surface of the acetabulum and implant therein an acetabular prosthesis. Preparation entails first of all a step of cleaning the bone, removing in particular the soft tissues and cartilage which preclude correct visualization of the bony landmarks (e.g. the acetabular fossa) present on the periphery of the acetabulum. So-called acetabular reaming is then performed, using a special tool inserted in the cavity. Acetabular reaming serves to smooth the internal surface of the cavity in order to prepare it to receive the acetabular prosthesis.

Another tool, called an impactor, is used to position and fix the acetabular prosthesis. This tool has a stem, to the end of which the replacement cotyle is fixed; it enables the prosthetic device both to be inserted in the bone cavity and mechanically locked in place before the stem is withdrawn.

The above-mentioned operations of preparing, positioning and fixing the acetabular prosthesis within the corresponding pelvic cavity are extremely critical and delicate steps in an arthroplasty procedure. The orientation of the acetabular prosthesis, which is defined by these operations, in fact largely determines the implant's success in the long term. A correct positioning will result in an optimal distribution of loads and an ideal stability of the prosthesis; an incorrect positioning, on the contrary, may result in a rapid deterioration of the implant or in biological complications of another kind.

It should be observed, moreover, that the aforesaid procedures are complicated by the difficult access to the bone site, and by the limited visibility of the latter. In particular, while in the hip arthroprosthesis operations the removal of the femoral neck serves in some way to make the route toward the acetabulum more pervious, in hip resurfacing arthroplasty the surgeon does not enjoy this relative advantage.

It may further be observed that the use of specific guides realized with rapid prototyping systems, currently applied in other orthopaedic surgical procedures, cannot be easily transferred to operations on the acetabulum. In fact, a vast, easily exposable bone area ensuring a stable positioning on the physical guide is lacking around the acetabular cavity.

International patent WO 2011/117644 proposes a set of instruments that the surgeon can use to perform operations on the acetabulum, comprising: locating means, temporarily located in the acetabulum; guide means, set in a pre-established position in relation to the locating means and serving as a guide, when in that position, for the instruments used to prepare of the acetabular surface (acetabular reamer) and position and fix the prosthesis (impactor); as well as support means for maintaining the guide means in that position when the locating means have been removed.

SUMMARY

Generally, a method is for implantation of an acetabular prosthesis. The method may include positioning an acetabular calibration guide at an acetabular cavity of a patient, and positioning an acetabular reference guide at a bone site of the patient separate from the acetabular cavity. The method may include aligning a calibration signal and a reference signal, the calibration and reference signals being respectively associated with the acetabular calibration guide and the acetabular reference guide. The method may include removing the acetabular calibration guide and positioning at least one tool at the acetabular cavity of the patient, and aligning a control signal and the reference signal for identifying a desired orientation of the at least one tool relative to the acetabular cavity, the control signal being associated with the at least one tool.

The method may also include reaming the acetabular cavity of the patient after removing the acetabular calibration guide. The method may comprise providing a target screen for the aligning of the calibration signal and the reference signal and the aligning of the control signal and the reference signal. The aligning of the calibration signal and the reference signal and the aligning of the control signal and the reference signal each may comprise aligning signals at a same point on the target screen. The aligning of the calibration signal and the reference signal and the aligning of the control signal and the reference signal may each comprise aligning respective optical emitter projections. The aligning of the calibration signal and the reference signal may be for identifying a desired orientation of the acetabular calibration guide.

In some embodiments, the acetabular calibration guide may comprise a positioning base configured to mate with the acetabular cavity of the patient, and the positioning base may include a supporting foot configured to abut against an internal surface of the acetabular cavity, and a plurality of positioning arms configured to engage with different points on a periphery of the acetabular cavity. The method may also include inserting a central positioning arm from the plurality of positioning arms in an acetabular fossa. The method may also include abutting a lower positioning arm from the plurality of positioning arms against a lower acetabular lip, and abutting an upper positioning arm from the plurality of positioning arms against an upper acetabular lip of the acetabular cavity.

The method may also include attaching respective optical emitters to the at least one tool, the acetabular calibration guide, and the acetabular reference guide. The method may include creating an incision at the acetabular cavity of the patient and cleaning a bone site of the acetabular cavity of the patient before the positioning of the acetabular calibration guide.

BRIEF DESCRIPTION OF THE DRAWINGS

FIG. 14 represents a perspective view of a connector and of a detail of an acetabular reference guide belonging to the set of instruments according to the present invention;

FIG. 17 represents a second step of a surgical method implemented by means of the set of instruments according to the present invention;

FIG. 18 represents a third step of a surgical method implemented by means of the set of instruments according to the present invention.

DETAILED DESCRIPTION

Figure 1:
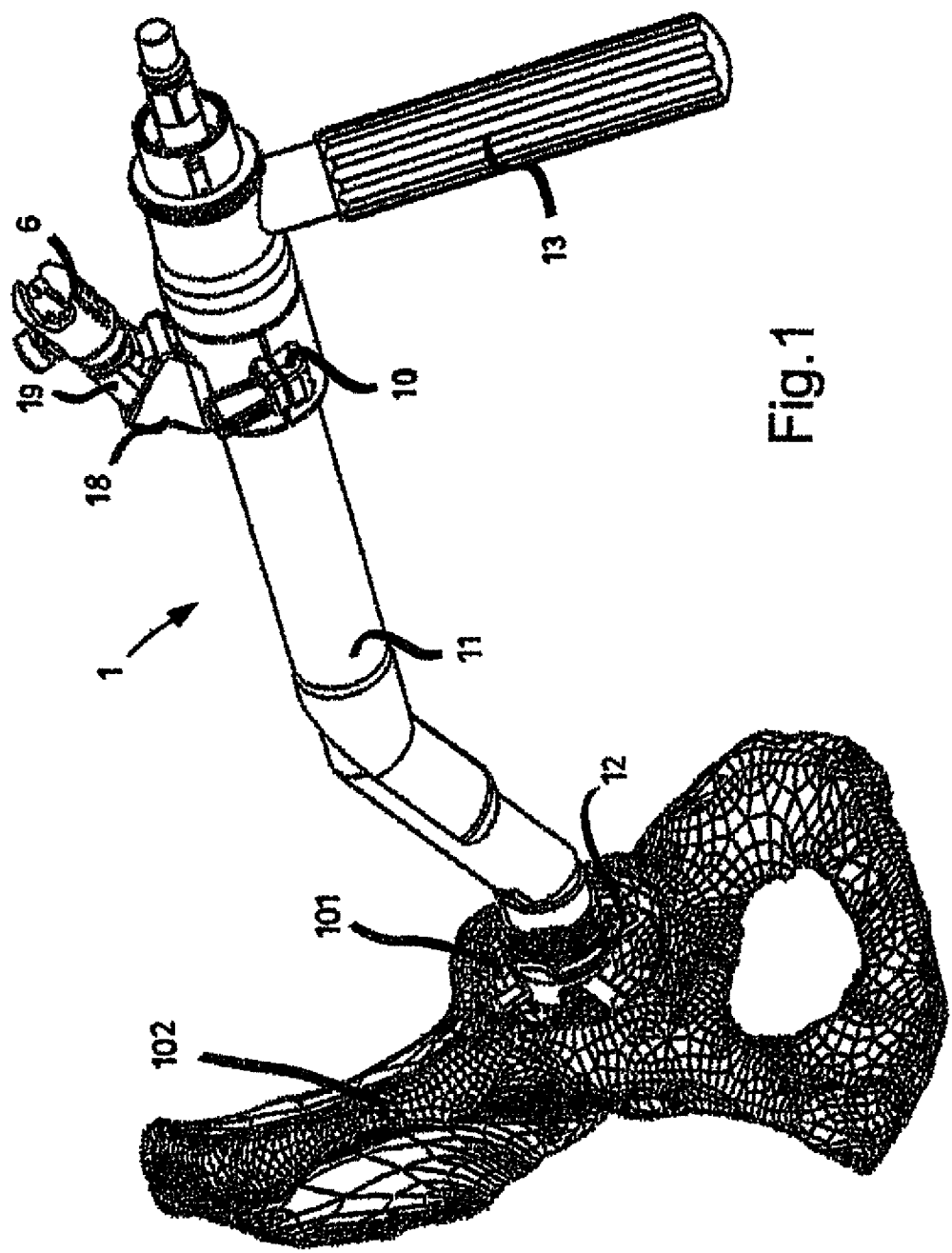
FIG. 1 represents a perspective view of a first tool and a connector associated therewith, belonging to the set of instruments according to the present invention, the first tool being engaged on a bone site of the patient according to one use configuration.

The aforesaid set of instruments, though satisfactory in certain respects, is clearly very complex in its use. The aforesaid guide means also have a considerable bulk, which may hamper the surgeon during his/her operation. The technical problem at the basis of the present invention is thus to devise set of instruments that enables a correct positioning of the tools for preparing the acetabular cavity and positioning an acetabular prosthesis, and which is more compact and simpler to use than prior art devices.

The aforesaid technical problem is solved by a set of instruments for the implantation of an acetabular prosthesis, comprising: at least one tool designed to operate in the acetabular cavity of a patient; at least one emitter, jointly associable with the tool and designed to emit a control signal to be aligned with a reference signal that identifies a correct orientation of the tool relative to the acetabular cavity.

In a preferred embodiment, the emitter includes an optical collimator, for example a laser projector, configured to emit an optical control signal, for example a laser beam. The optical control signal can be aligned with a reference optical signal, including, for example, of a second laser beam, so as to collimate the spots of the two signals projected onto a target surface.

It should be noted, moreover, that the possibility of using other prior art technologies for generating and aligning control and reference signals is not ruled out. For example, such signals could be represented by ultrasound waves that are aligned by equalizing the reflection times relative to a target surface.

As may be easily understood by a person skilled in the art, the alignment of the optical collimator with a reference optical signal provides a simple guide system for the surgical tools used to implant the acetabular prosthesis, thus defining an advantageous alternative to the physical guide structures known in the art. By aligning the light beam of the collimator with the reference signal, the surgeon can in fact control the degree of rotational freedom of a tool whose operating head is inserted into the acetabular cavity.

It should be noted that the same inventive idea is applicable, mutatis mutandis, to any other technologies for generating and aligning the signals that might be used. Moreover, it should be noted that the inventive idea can similarly be applied to the various tools subsequently used to prepare the acetabular cavity and in the subsequent steps of inserting and fixing the acetabular prosthesis. Such tools may include, for example, an acetabular reamer and/or an impactor for the acetabular prosthesis to be implanted.

It may be noted that the reference signal can be obtained and maintained with different methods. If an optical collimator is used to generate an optical control signal, the corresponding reference optical signal can be processed, for example, by means of software using images of the bone site of the patient and projected onto a target surface.

Preferably, however, the reference signal is obtained with a second emitter, which is jointly associated with a bone structure of the patient that is not involved in the operation of the surgical tools to be oriented. The set of instruments thus comprises an acetabular reference guide fixable to a bone site of the patient which is separate from the acetabular cavity and with which a second emitter designed to emit the reference signal can be jointly associated. Preferably, the bone site is chosen on the same hip bone that has the acetabular cavity.

In the preferred case of an optical collimator used to generate the (optical) control signal, an optical collimator (for example, a laser projector) is used in the same way to generate the reference signal. The above-mentioned solution has the advantage of providing a reference relative to the patient's hip bone, so that any movements of the bone do not prejudice the correct calibration of the reference provided.

The set of instruments according to the present invention can advantageously comprise an acetabular calibration guide that can be transitorily associated with the patient's acetabular cavity according to a desired orientation, the acetabular calibration guide being jointly associable with an emitter designed to emit a calibration signal which identifies the orientation of the acetabular guide itself, the reference signal being able to be aligned with the calibration signal.

Once again, in the preferred case of an optical collimator used to generate the (optical) control and reference signals, an optical collimator (for example a laser projector) is used in the same way to generate the calibration signal. The acetabular calibration guide can be represented, in particular, by a physical structure, preferably rod-shaped, which is temporarily inserted into the acetabular cavity. Once the desired orientation for the rod-shaped structure has been reached, the signal emitted by the emitter associated with it enables the reference signal provided by the second emitter to be calibrated. Therefore, once the acetabular calibration guide has been removed, the remaining reference guide, jointly implanted in a portion of bone at a distance from the acetabulum, enables the orientation previously assumed by the rod-shaped structure to be exactly replicated.

The acetabular calibration guide can comprise, in particular, a positioning base that precisely mates with the patient's acetabular cavity. This positioning base can be realized, for example, on the basis of tomographic images of the bone site acquired prior to surgery.

The acetabular base enables a specific planned orientation to be immediately replicated, possibly with the aid of software for the three-dimensional graphics, in the preoperative phase. The positioning base can have, in particular, a supporting foot intended to abut against the internal surface of the acetabular cavity, and a plurality of positioning arms intended to engage with different points on the periphery of the acetabular cavity.

A central positioning arm can, for example, be intended to be inserted in the acetabular fossa, a lower positioning arm to abut against the lower acetabular lip and an upper positioning arm to abut against the upper acetabular lip of the acetabular cavity. It should be noted that the same emitter, including in particular an optical collimator in a preferred embodiment of the present invention, can be alternatively associated with different tools (acetabular reamer, impactor) and with the acetabular calibration guide. The second emitter, associated with the acetabular reference guide, can also be of a type that is identical to the first and interchangeable with it.

The emitter is preferably mounted on a connector, configured to be snap-fitted to adaptors integral with the various tools as well as on an adaptor integral with the acetabular calibration guide. The same emitter can thus be used in the subsequent steps of calibrating, reaming and implanting the acetabular prosthesis, while a setting of the emitter relative to the connector is maintained unchanged.

The same connector can also be snap fitted to an adaptor integral with the acetabular reference guide; in this case, as previously suggested, the two emitters with the respective connectors are interchangeable with each other. The emitters can thus be associated with connectors configured to be fitted to specific adaptors integral with the various components of the set of instruments. In particular, the emitter is preferably associated with the connector by means of a pivotable joint in order to facilitate calibration of the reference signal. The emitter can further comprise a locking screw serving to selectively block the rotation of the pivotable joint once the desired calibration has been reached.

Figure 2:
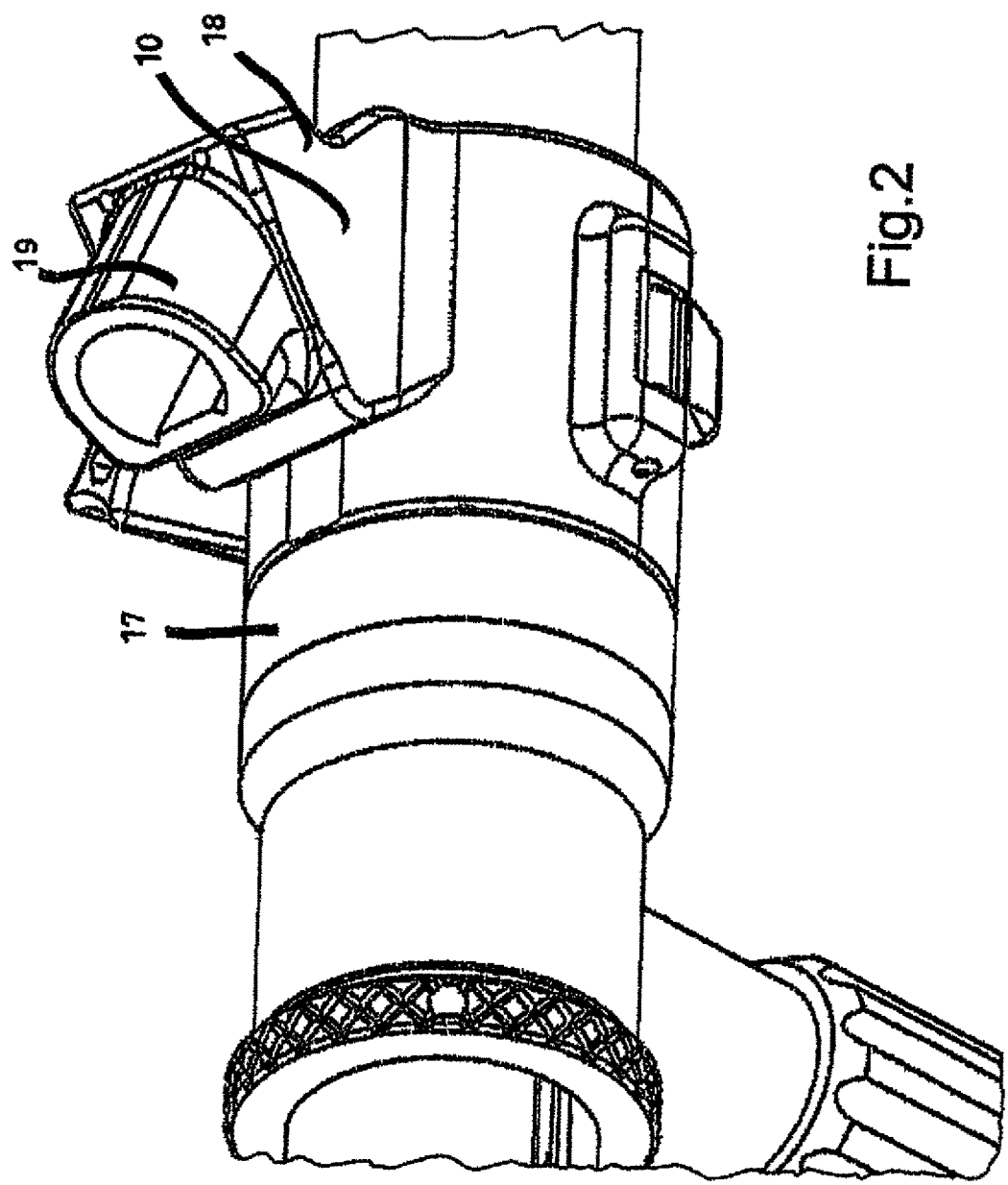
FIG. 2 represents a perspective view of a detail of the first tool in FIG. 1, without the associated connector.
Figure 3:
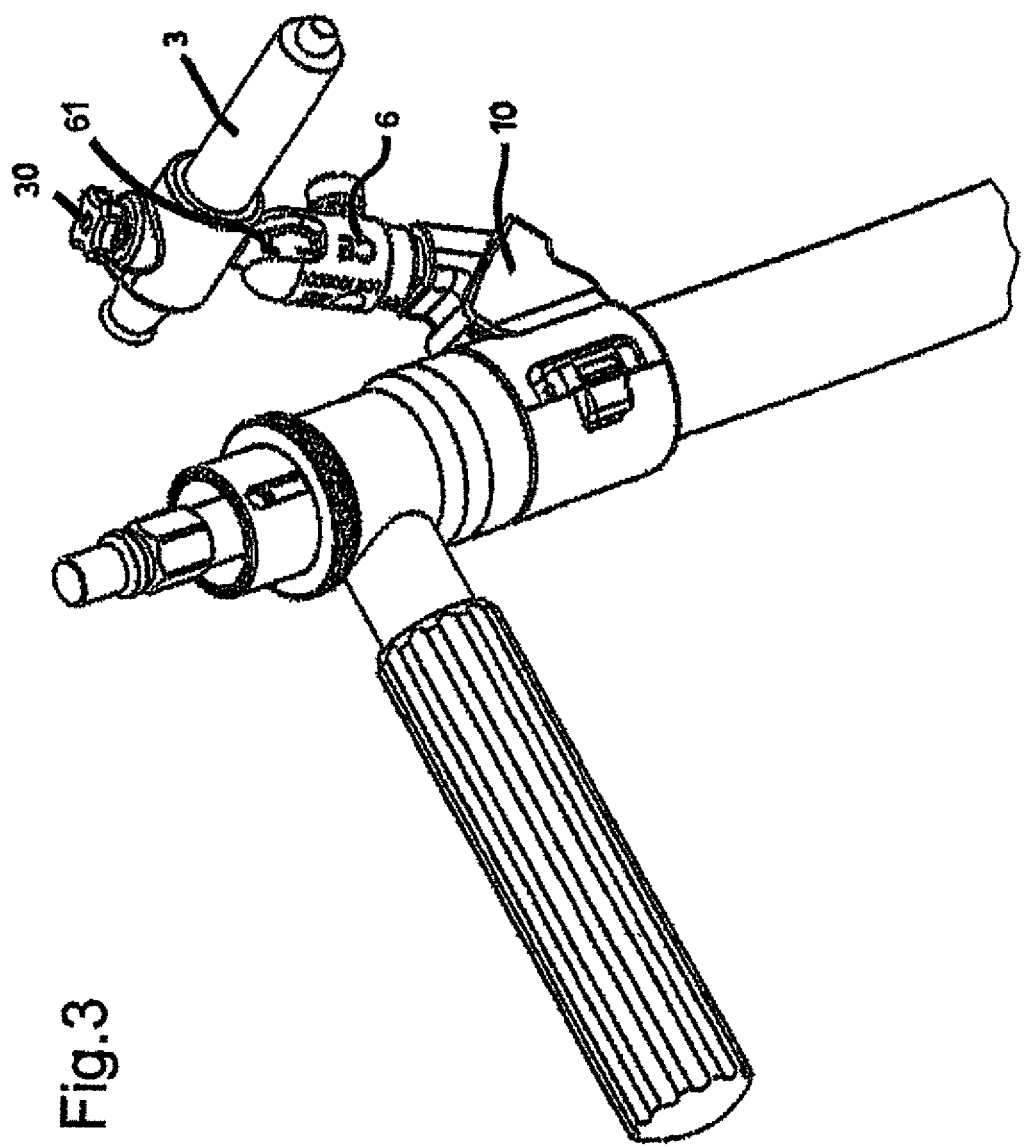
FIG. 3 represents a perspective view of the first tool in FIG. 1, with an optical collimator associated with the connector.
Figure 5:
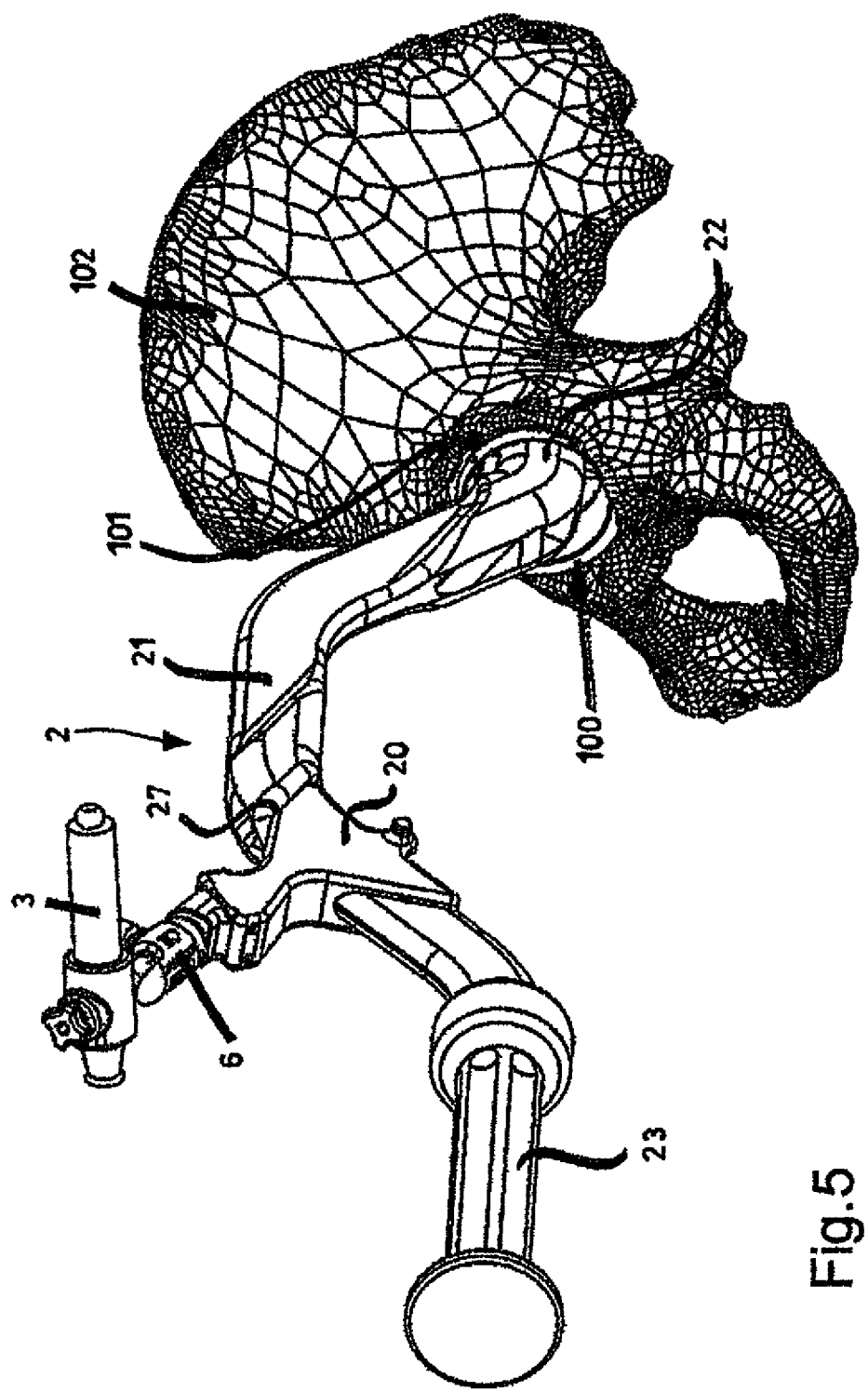
FIG. 5 represents a perspective view of a second tool and an optical collimator associated with it by means of a connector, both belonging to the set of instruments according to the present invention, the second tool being engaged on a bone site of the patient according to one use configuration.
Figure 6:
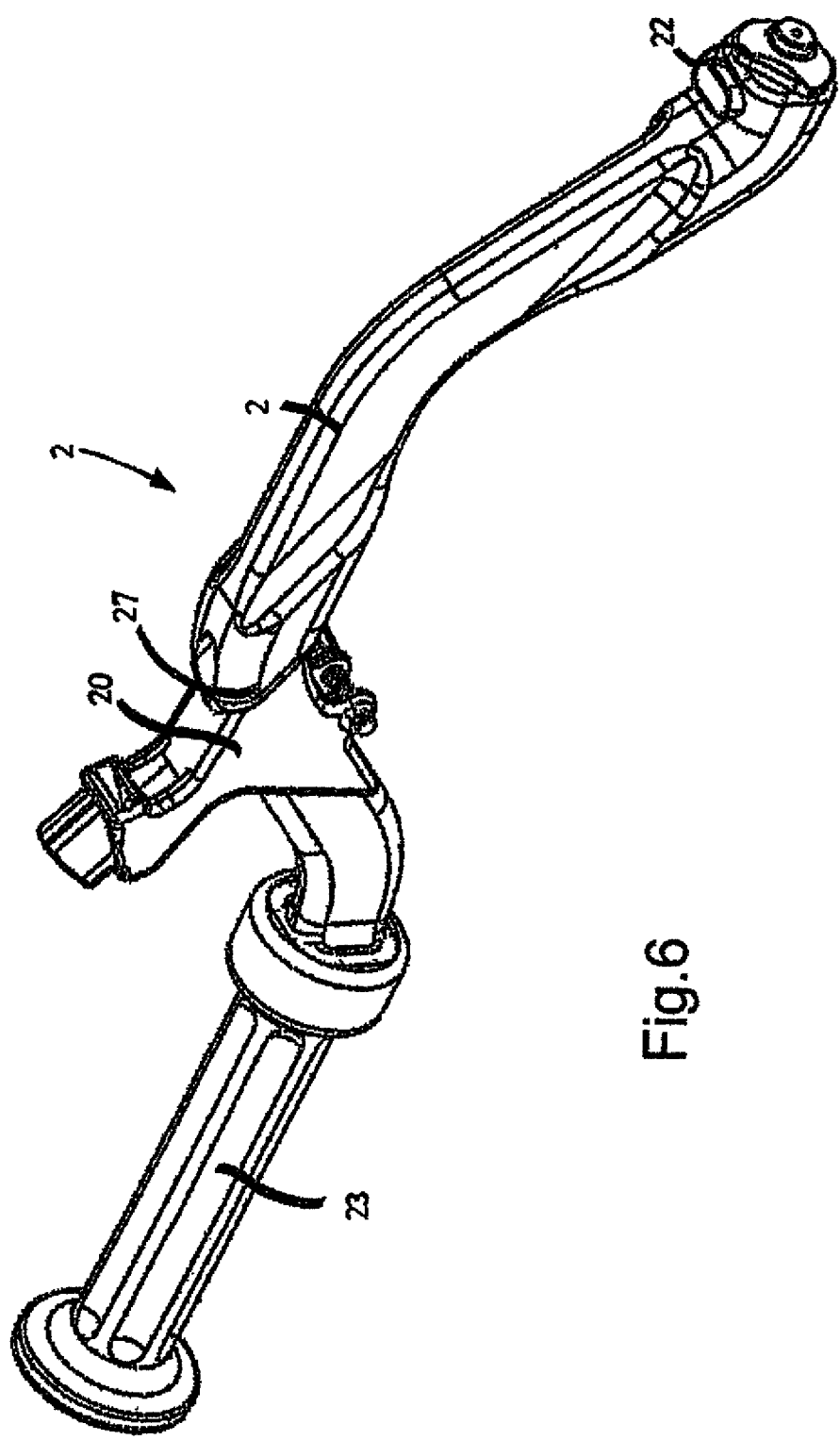
FIG. 6 represents a perspective view of the second tool in FIG. 5, without the associated connector.

The set of instruments according to the present invention comprises the following components, broadly described below: an acetabular reamer 1, individually represented in the appended FIGS. 1-3; an impactor 2, individually represented in the appended FIGS. 5-6; and an acetabular calibration guide 5, individually represented in the appended FIGS. 8-13.

Figure 15:
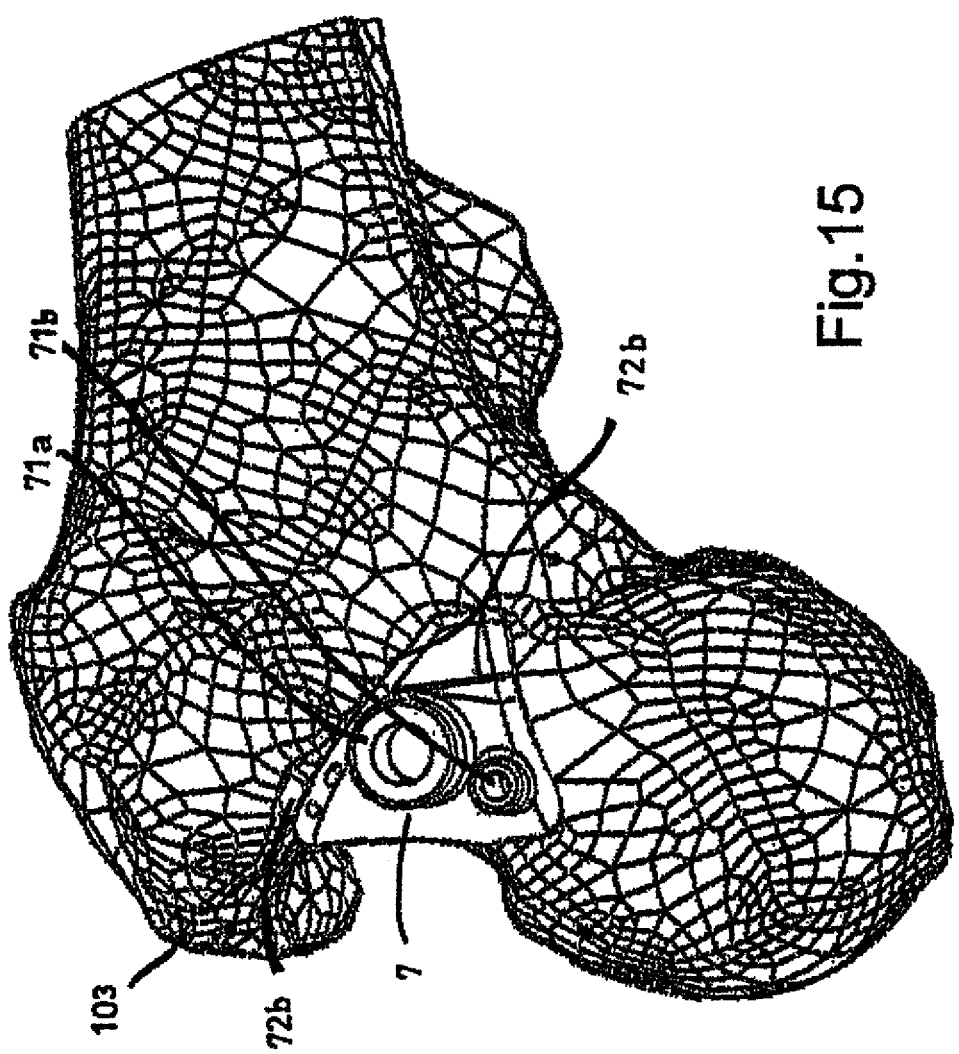
FIG. 15 represents a perspective view of a femoral guide belonging to the set of instruments according to the present invention.
Figure 16:
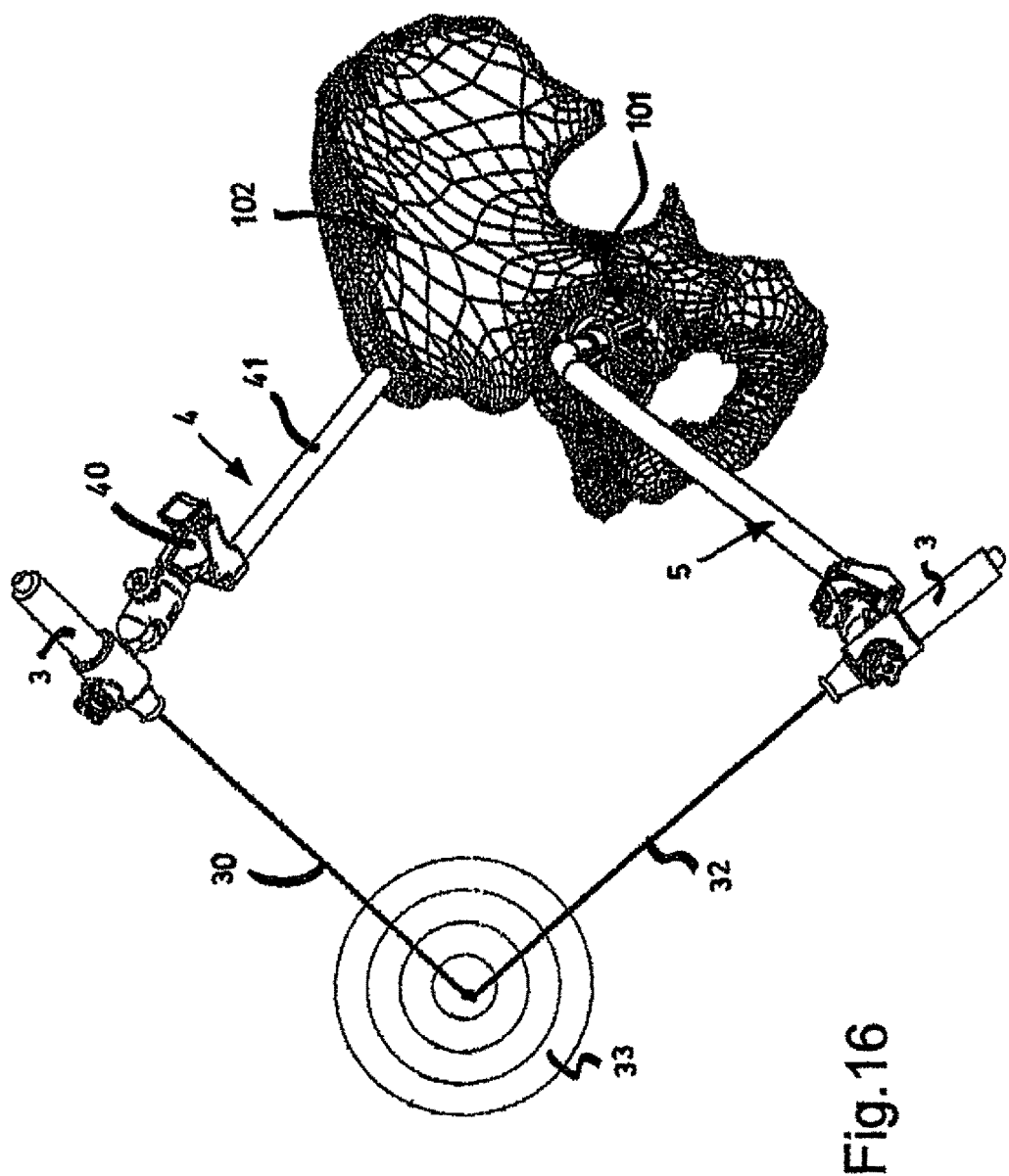
FIG. 16 represents a first step of a surgical method implemented using the set of instruments according to the present invention.

The set of instruments further comprises an acetabular reference guide 4, which may be seen in the overall FIGS. 16-18; and at least two emitters, represented in particular by optical collimators 3, identical to each other and associable with connectors 6. The set of instruments can comprise, finally, a femoral guide 7, individually represented in the appended FIG. 15.

The components listed above, with the exception of the femoral guide 7, are used in sequence, according to the procedures described below, in order to implant an acetabular prosthesis 100, which is known in itself, inside the acetabular cavity 101 of the hip bone 102 of a patient. The femoral guide 7 is used, on the other hand, to perform the resections and drilling operations necessary to implant a prosthestic femoral component cooperating with the acetabular prosthesis 100.

In the preferred embodiment represented here, the acetabular reamer 1 comprises a stem 11 having a split form, provided on one end with a head 12 for mounting a reamer, and at the opposite end with a lateral Chana type handle 13. At the point of attachment of the lateral handle 13, an adaptor 10 is fitted over the stem, the adaptor being configured to receive one of the connectors 6 of the optical collimators 3.

Figure 4:
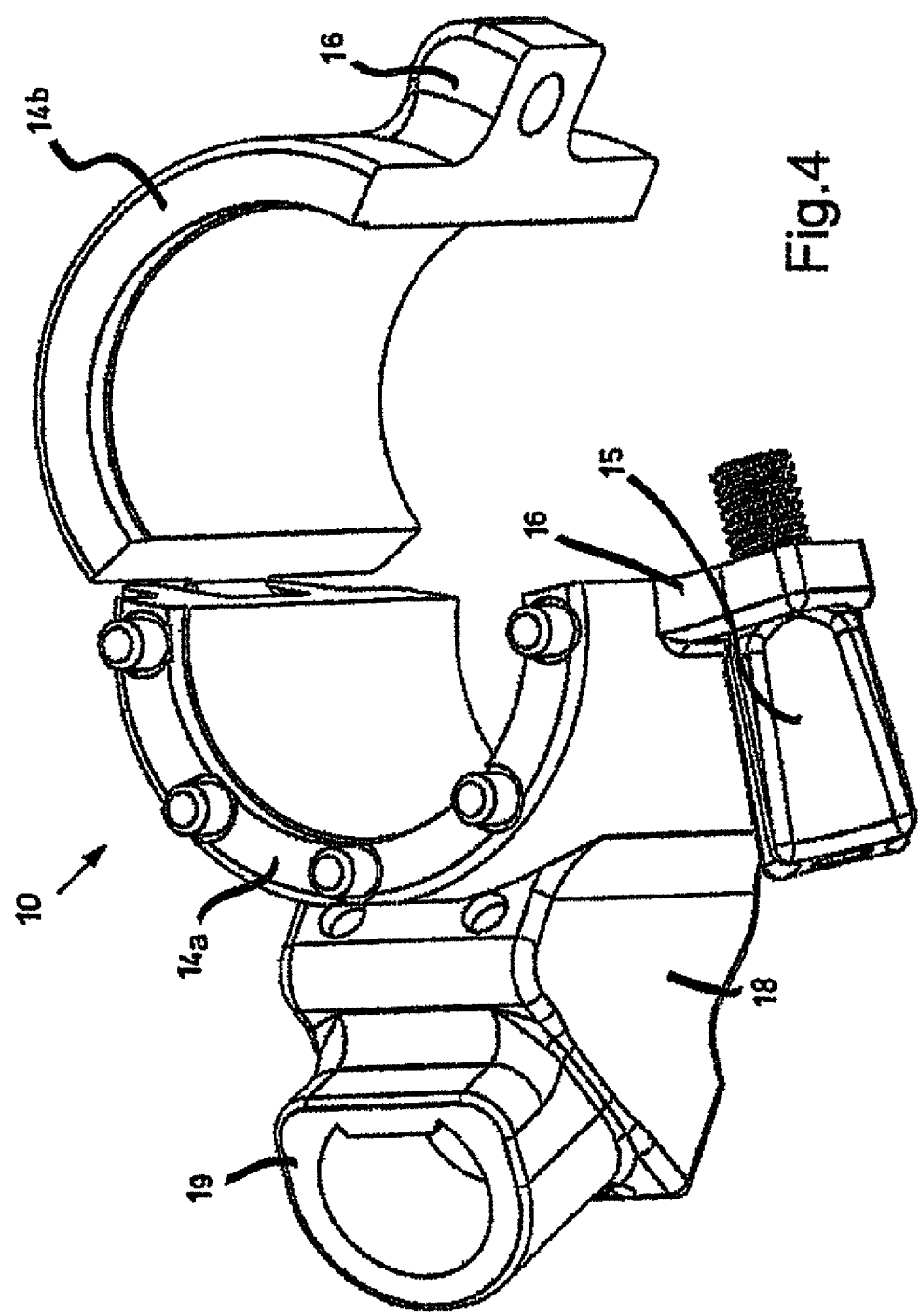
FIG. 4 represents a perspective view of an adaptor belonging to the first tool in FIG. 1.

The adaptor 10, individually shown in FIG. 4, comprises a collar-type coupling composed of two semi-cylindrical portions 14a; 14b hinged together. The two semi-cylindrical portions 14a; 14b are configured to encircle a rectilinear portion of the stem 11 of the acetabular reamer, abutting beneath a shoulder 17. The closure of the collar-type coupling is assured by a fastening screw 15, which passes through lateral flanges 16 of the two semi-cylindrical portions 14a; 14b. Integral with the attachment collar, there is a wedge-like portion 18 of the adaptor 10, which bears a female coupling 19 intended to enable the snap fitting of a corresponding male coupling 62 of the connector 6.

In the preferred embodiment represented here, the impactor 2 comprises a stem 21 having a split form and provided on one end with a head 22 suitable for carrying an acetabular prosthesis 100, and on the opposite end with a longitudinal handle 23. The stem 21 has an oblique distal portion which follows the longitudinal handle 23, then a longitudinal portion parallel to the handle 23, and, finally, a proximal oblique portion which ends with the head 22, aligned with the handle 23.

Figure 7:
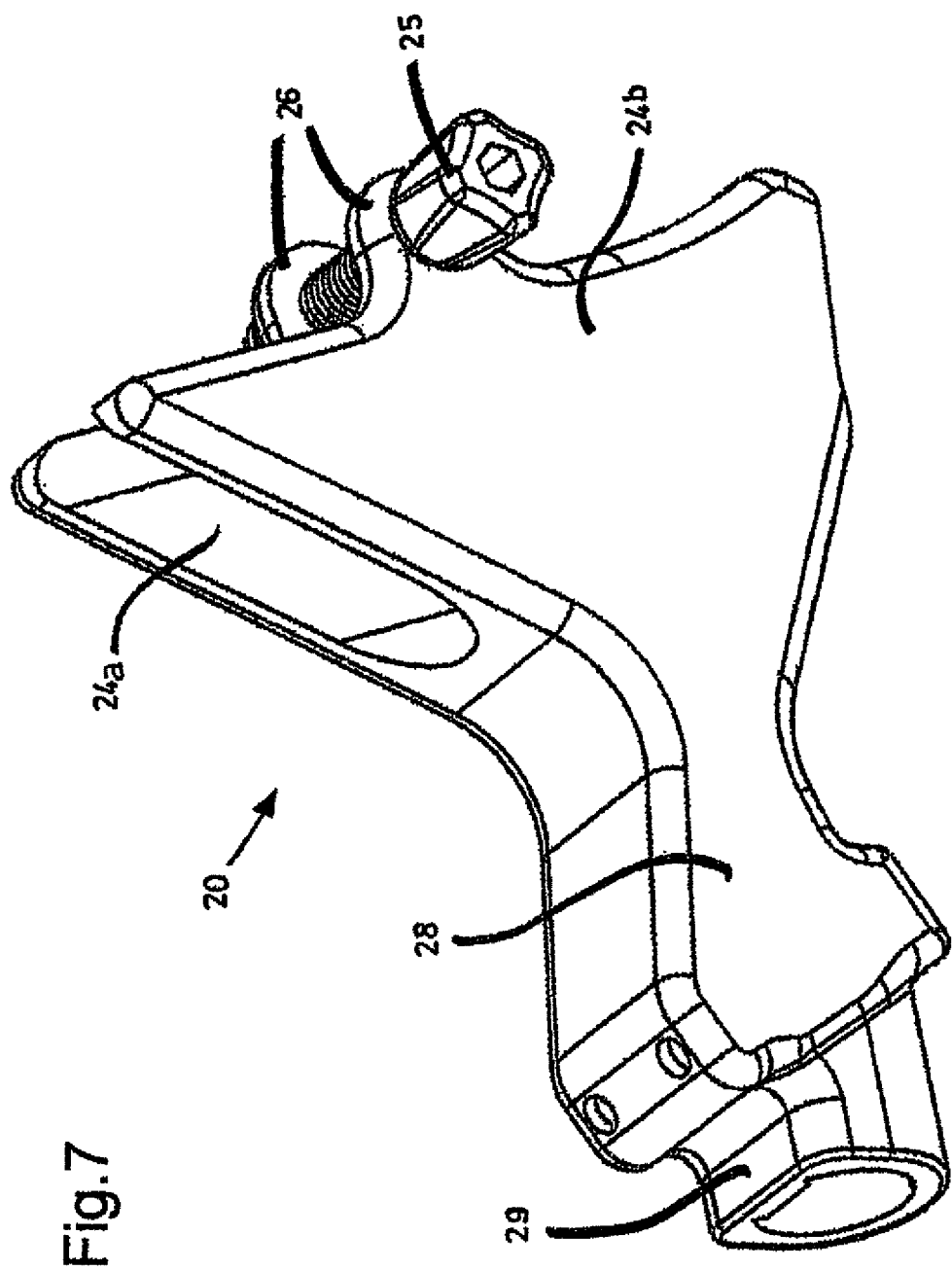
FIG. 7 represents a perspective view of an adaptor belonging to the second tool in FIG. 5.
Figure 8:
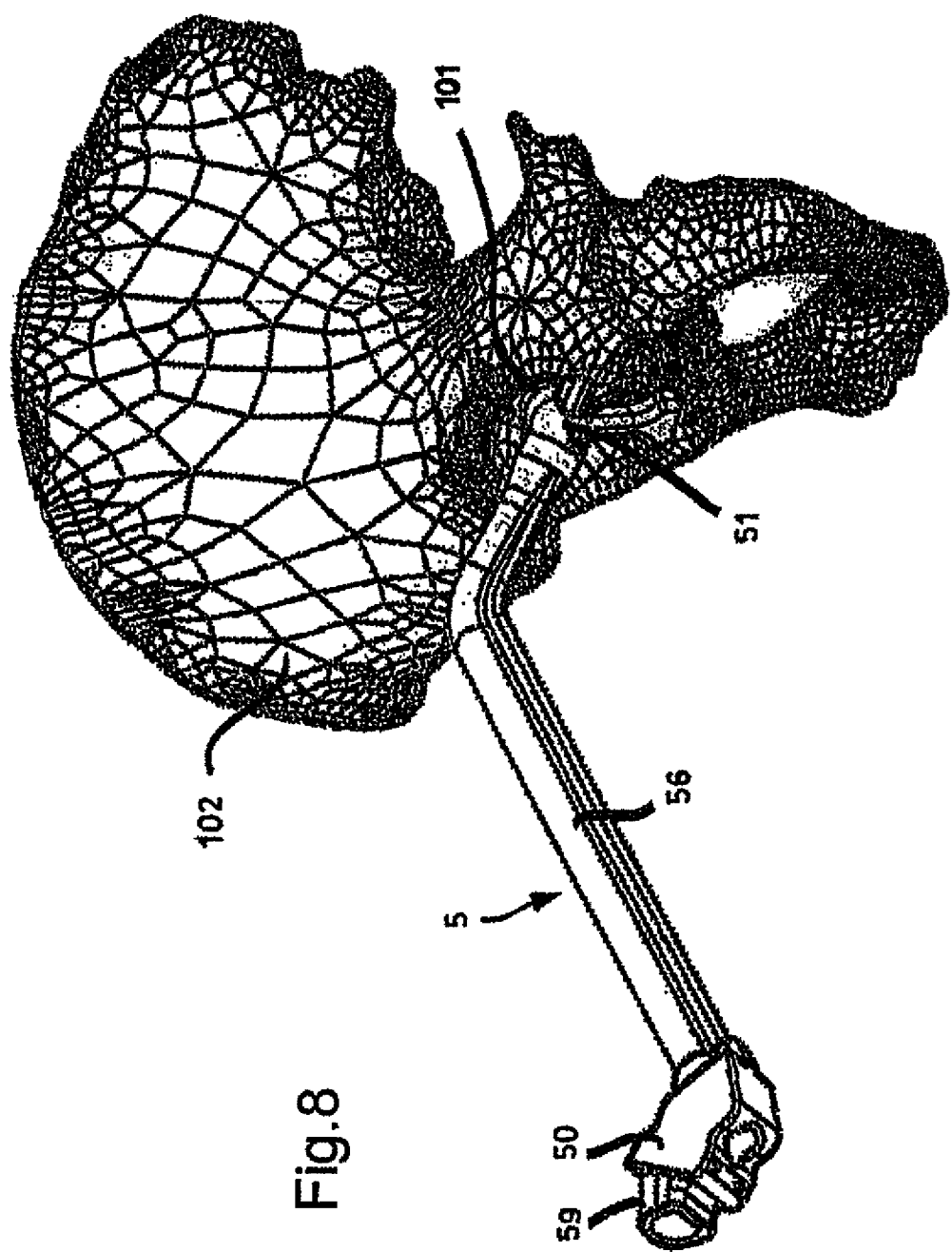
FIG. 8 represents a perspective view of an acetabular calibration guide, belonging to the set of instruments according to the present invention, engaged on a bone site of the patient according to one use configuration.
Figure 9:
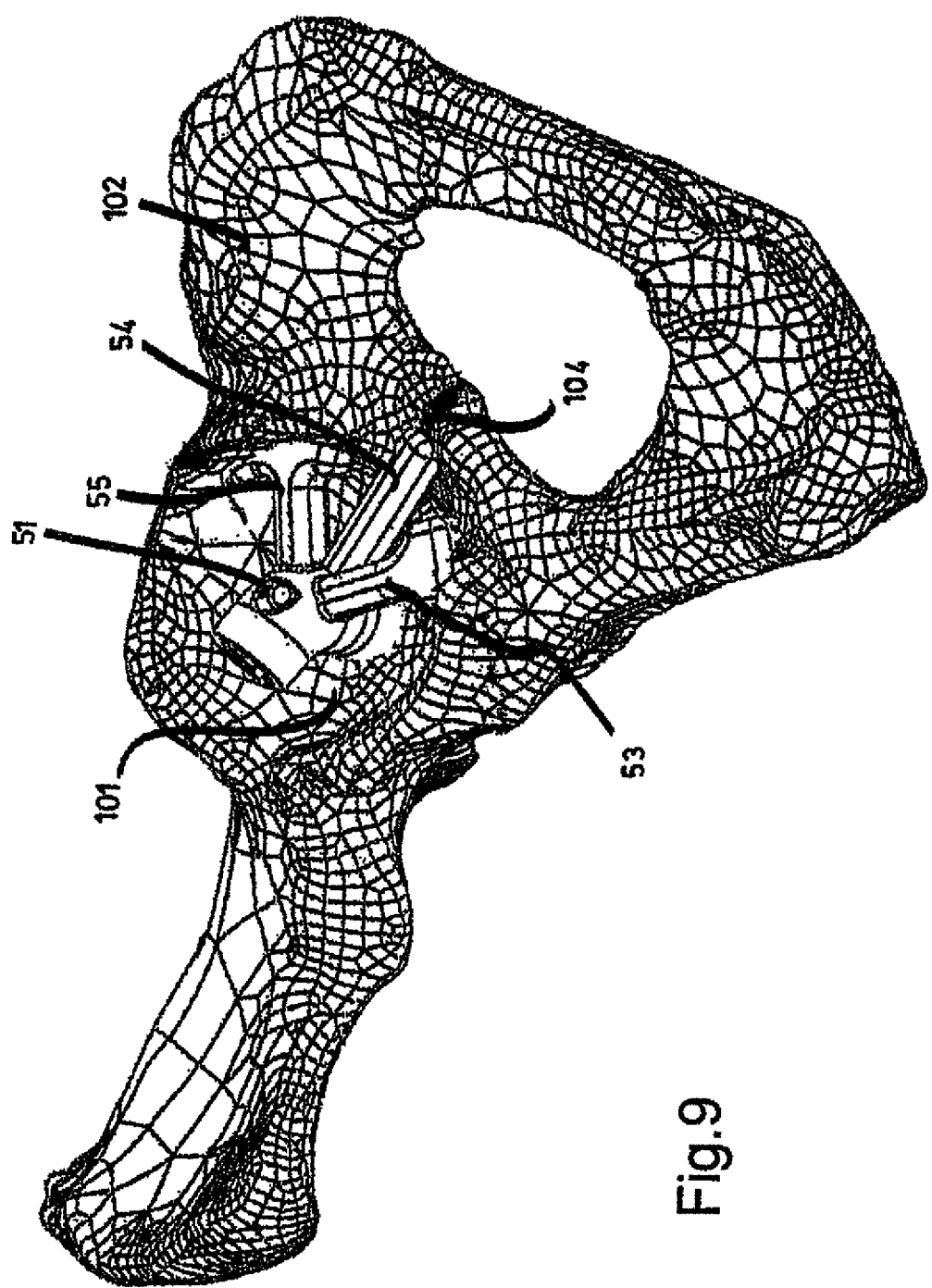
FIG. 9 represents a perspective view of a positioning base, belonging to the acetabular calibration guide in FIG. 8, engaged on a bone site of the patient according to one use configuration.
Figure 10:
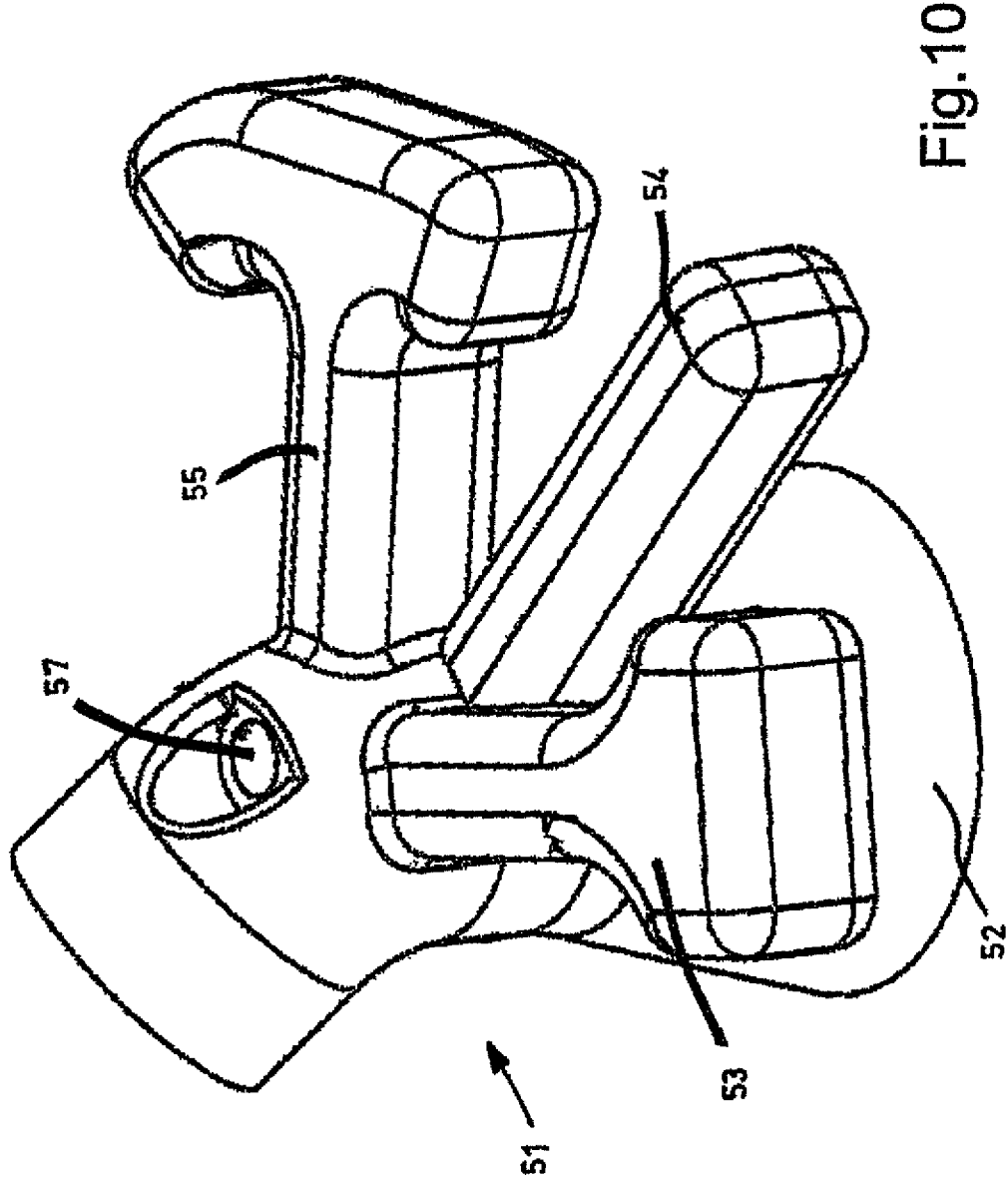
FIG. 10 represents a perspective view of the positioning base in FIG. 9, dissociated from the bone site of the patient.
Figure 11:
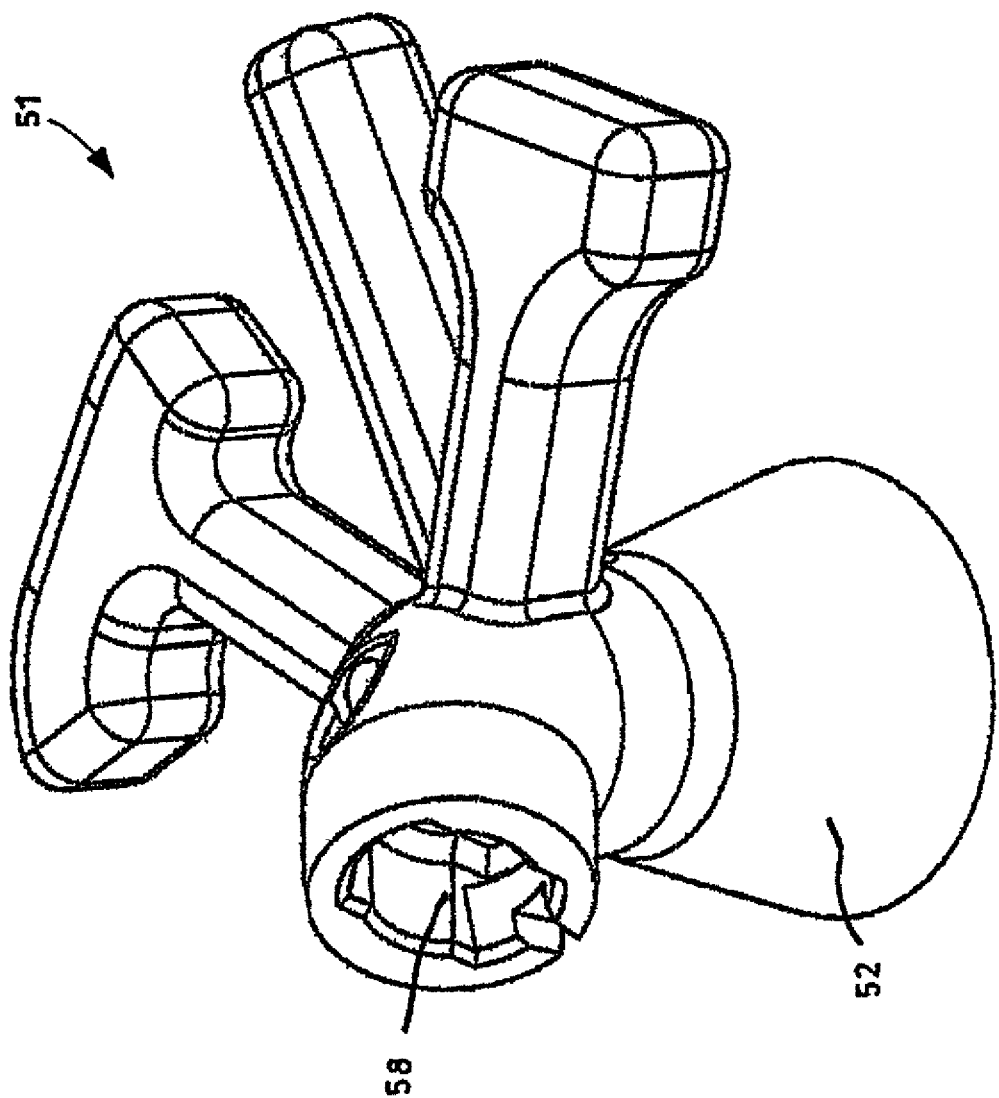
FIG. 11 represents a perspective view, from a different angle, of the positioning base in FIG. 10.

In correspondence of the oblique distal portion 23, an adaptor 20 is fitted over the stem 21, the adaptor being configured to receive one of the connectors 6 of the optical collimators 3. The adaptor 20, individually shown in FIG. 7, comprises a forked connector composed of two elastic walls 24a; 24b connected to a same main body 28. The two elastic walls 24a; 24b are configured to grasp the distal oblique portion 23 of the impactor 2, abutting below a shoulder 27. The closure of the forked connector is assured by a connecting screw 25, which passes through two end flanges 26 formed on the two elastic walls 24a; 24b.

Opposite the elastic walls 24a; 24b, the main body 28 has a female coupling 29 intended to enable the snap fitting of a corresponding male coupling 62 of the connector 6. The acetabular reference guide 4 takes the form of a supporting frame implantable on the hip bone 102 and intended to support one of the optical collimators 3. It comprises, in particular, a rectilinear stem 41, which is directly implantable on the patient's bone and has an adaptor 40 on one end, configured to receive one of the connectors 6 of the optical collimators 3.

The adaptor 40, represented in FIG. 14 together with the connector 6, comprises in particular a female coupling 49 intended to enable the snap fitting of a corresponding male coupling 62 of the connector 6. The adaptor 40 also has a release button 48, which enables the release of the male coupling 62. The acetabular calibration guide 5 includes a supporting frame transitorily associable with the acetabular cavity 101 of the patient according to a desired orientation and intended to support one of the optical collimators 3.

The acetabular calibration guide 5 comprises, in particular, an elbow-shaped stem 56, a positioning base 51 mounted on the proximal end of the stem 56 and an adaptor 50, which is configured to receive one of the connectors 6 of the optical collimators 3 and mounted on the distal end of the stem 56. The positioning base 51 is configured to mate precisely with the acetabular cavity 101 of the patient; in order to achieve this purpose, it is preferably designed on the basis of tomographic images acquired prior to surgery.

The positioning base 51 has a supporting foot 52 intended to abut against the internal surface of the acetabular cavity 101. In a distal position relative to the supporting foot 52, at the edge of the acetabular cavity 101, three positioning arms branch off: an upper positioning arm 53 intended to abut against the upper acetabular lip, a central positioning arm 54 intended to be inserted into the acetabular fossa 104 and a lower positioning arm 55 intended to abut against the lower acetabular lip.

The upper 53 and lower 55 positioning arms are coplanar and at an angle relative to each other that can range from 50 to 200 degrees; the central positioning arm 54, which lies in a plane that is slightly proximal relative to that of the other two arms 53; 55, is in an intermediate angular position between them.

It should be noted, moreover, that whereas the upper 53 and lower 55 positioning arms have a free T-shaped end, the central arm 54 does not have an enlarged end. The planar extension of the T-shaped ends follows the profile of the acetabular lips; it may be observed that the end of the lower arm 55 has a greater extension than the corresponding end of the upper arm 53.

Figure 12:
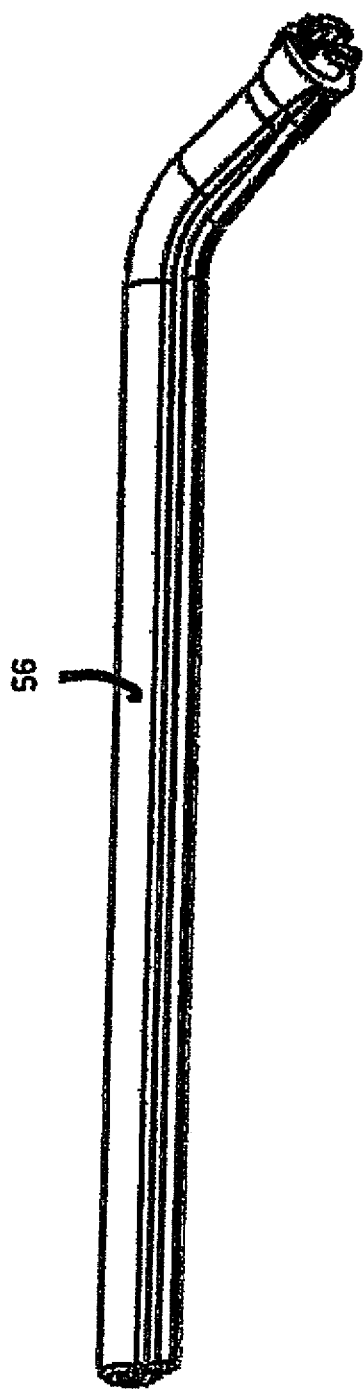
FIG. 12 represents a perspective view of a stem belonging to the acetabular calibration guide in FIG. 8.
Figure 13:
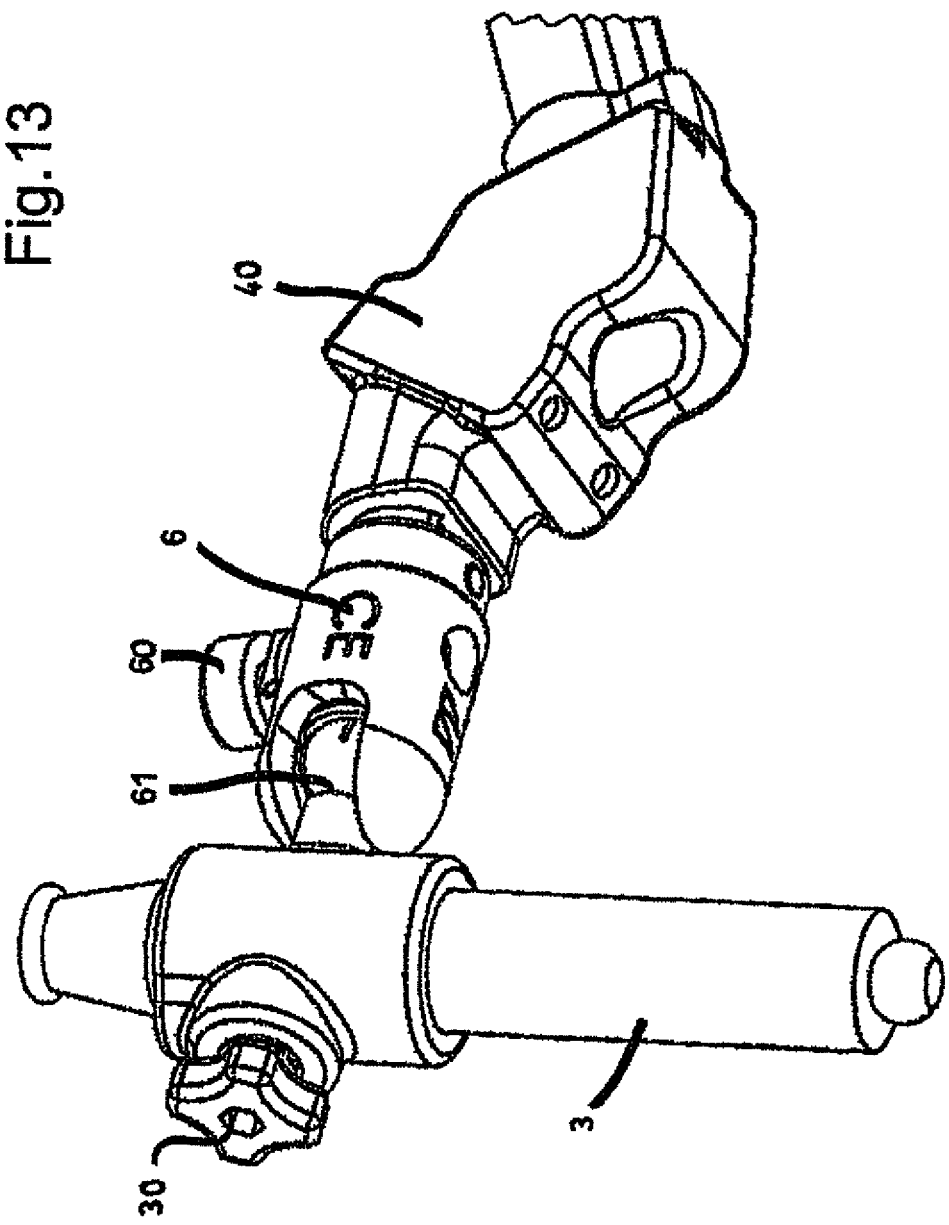
FIG. 13 represents a perspective view of a detail of the acetabular calibration guide in FIG. 8, associated by means of a connector to an optical collimator.

Above the positioning base 51 there is provided a through hole 57, which passes through the supporting foot 52 to permit the insertion of a pin for temporary fixation to the patient's bone. Above the positioning base 51 there is also provided an insertion socket 58 oriented at 45° relative to the extension of the supporting foot 52; the proximal end of the elbow-shaped stem 56, shown in detail in FIG. 12, is intended to be snap fitted into the insertion socket 58.

It should be noted that the curvature of the elbow-shaped stem 56 is such that the proximal portion of the stem is substantially aligned with the supporting foot 52. The adaptor 50, mounted on the distal end of the elbow-shaped stem 56, comprises in particular a female coupling 59 intended to enable the snap fitting of a corresponding male coupling 62 of the connector 6.

The connector 6, which may be seen in detail in FIG. 14, has a male coupling 62 that can be snap fitted into any female coupling 19; 29; 49; 59 present on the adaptors 10; 20; 40; 50 described previously. It should be noted that the male coupling 62 and the female couplings 19; 29; 49; 59 have an eccentric structure so as to preclude the relative rotation of the components associated by means of a snap fit.

It may be noted that the configuration of the instruments and of the couplings is such that the female couplings 19; 29; 59 respectively associated with the acetabular reamer 1, the impactor 2 and the acetabular calibration guide 5 have an identical position and orientation, in the operative configuration, relative to the acetabular cavity 101.

The connector 6 comprises a main body 63, which has the male coupling 62 at one of its ends and a pivotable joint 61 at the opposite end. The pivotable joint 61 includes in particular a ball pivotably housed in a U-shaped seat of the main body 63. The pivotable ball can be associated, by means of a screw integral with a tightening knob 30, with the optical collimator 3, represented in this case by a laser projector with an elongated shape.

Thanks to the pivotable joint 61, it is thus possible to modify the orientation of the laser projector relative to the main body 63 of the connector 6 which supports it. A locking screw 60 which passes through the main body 63 of the connector 6 enables the aforesaid pivotable joint 61 to be locked in the desired position, so as to fix the position of the laser projector relative to the main body 63.

The femoral guide 7, which can be part of the set of instruments according to the present invention, comprises holes 71a for connecting with a manual support pin and 71b for the insertion of a temporary fixing pin. The surface 72a represents the cutting surface on which the surgeon can rest the instrument for resecting the femoral bone 103. Present on the surface 72a there is a block 72b for limiting the extent of the cut in order to preserve the greater trochanter.

We shall now go on to describe, with specific reference to the appended FIGS. 16-18, a surgical method for the implantation of an acetabular prosthesis according to the present invention. In a first step of the method, following the traditional operations of incision and preliminary cleaning of the bone site, one proceeds to position the acetabular calibration guide 5.

As previously discussed, the acetabular calibration guide can be associated with the acetabular cavity 101 of the patient in a precise position so as to define a desired orientation for the tools which will be subsequently used on the same bone site. In this step, the optical collimator 3 must be fixed to the acetabular calibration guide 5 by means of the connector 6. The optical collimator 3 projects an optical calibration signal 32, which serves to define a punctiform spot on a screen or another target surface 33.

It may be noted in FIG. 16 that the target screen 33 can includes a concentric target for evaluating the accuracy of alignment of two optical signals. Again in this step, one proceeds to implant the previously defined acetabular reference guide 4 on a portion of the patient's hip bone 102 at a distance from the acetabular cavity 101. A respective optical collimator 3 must be associated with this guide, too. The collimator 3 projects a reference optical signal 30, which serves to define a punctiform spot on the aforesaid target screen 33.

The method then envisages a step of calibrating the reference optical signal 31. To calibrate this signal, the punctiform spot defined on the target screen is collimated with the one defined by the optical calibration signal 32 previously defined, as shown in FIG. 16. The calibration can be performed by acting upon the pivotable joint 61 of the connector 6 associated with the acetabular reference guide 4.

Only after the reference optical signal 30 has been calibrated, the acetabular calibration guide 5 is extracted so as to disengage the acetabular cavity 101. Subsequently, the acetabular cavity 101 is reamed by means of the acetabular reamer 1, with which the optical collimator 3 previously fitted to the acetabular calibration guide 5 is associated. The optical signal projected by the optical collimator 3 now takes on a function of controlling the orientation of the tool, which is the reason why it will hereinafter be identified as an optical control signal 30.

In this step, the surgeon can use the reference optical signal 31 to orient the tool 1 in the desired direction, that is to say, in the direction initially assumed by the acetabular calibration guide 5. To achieve this, as illustrated in FIG. 17, it is sufficient to collimate the spot of the optical control signal 30 with that of the reference optical signal 31.

In fact, the morphological identicalness between the acetabular calibration guide 5 and acetabular reamer 1 ensures that, in the event of alignment, the optical control signal 30 will strike in the same point as the optical calibration signal 32, previously collimated with the reference optical signal 31.

In a subsequent step of applying the acetabular prosthesis 100, use is made of the previously described impactor 2, which is fitted with the optical collimator 3 previously used in combination with the acetabular calibration guide 5 and the acetabular reamer 1. In this case as well, as shown in FIG. 18, the surgeon has the possibility of easily aligning the tool 2 with the chosen spatial reference by collimating the punctiform spot generated by the optical control signal 30 with the spot due to the optical calibration signal 31.

It is wholly evident that the main advantage of the set of instruments according to the present invention lies in its singular structural simplicity. The advantage of minimal invasiveness in the surgical area is likewise important.

A further advantage lies in the fact that the surgeon is allowed ample freedom of action during the operations of preparing the acetabular surface. In fact, the surgeon can freely perform the preliminary roughing operations according to his/her personal skill and according to his/her perception of the circumstances, and then be guided by the laser beam emitted by the tool only on the occasion of the final finishing operations, aimed at achieving, with precision, the final shape in the exact position desired.

Obviously, in order to satisfy specific contingent requirements, the person skilled in the art may introduce numerous modifications and variants to the above-described set of instruments, all remaining within the scope of protection of the invention as defined in the following claims.

That which is claimed is:

1. A method for implantation of an acetabular prosthesis, the method comprising:
    positioning an acetabular calibration guide at an acetabular cavity of a patient;
    positioning an acetabular reference guide at a bone site of the patient separate from the acetabular cavity;
    aligning a calibration signal and a reference signal, the calibration and reference signals being respectively associated with the acetabular calibration guide and the acetabular reference guide;
    removing the acetabular calibration guide and positioning at least one tool at the acetabular cavity of the patient; and
    aligning a control signal and the reference signal for identifying a desired orientation of the at least one tool relative to the acetabular cavity, the control signal being associated with the at least one tool;
    wherein the acetabular calibration guide comprises a positioning base configured to mate with the acetabular cavity of the patient; and
    wherein the positioning base includes a supporting foot configured to abut against an internal surface of the acetabular cavity, and a plurality of positioning arms configured to engage with different points on a periphery of the acetabular cavity.

2. The method according to claim 1 further comprising reaming the acetabular cavity of the patient after removing the acetabular calibration guide.

3. The method according to claim 1 further comprising providing a target screen for the aligning of the calibration signal and the reference signal and the aligning of the control signal and the reference signal.

4. The method according to claim 3 wherein the aligning of the calibration signal and the reference signal and the aligning of the control signal and the reference signal each comprises aligning signals at a same point on the target screen.

5. The method according to claim 1 wherein the aligning of the calibration signal and the reference signal and the aligning of the control signal and the reference signal each comprises aligning respective optical emitter projections.

6. The method according to claim 1 wherein the aligning of the calibration signal and the reference signal is for identifying a desired orientation of the acetabular calibration guide.

7. The method according to claim 1 further comprising inserting a central positioning arm from the plurality of positioning arms in an acetabular fossa.

8. The method according to claim 1 abutting a lower positioning arm from the plurality of positioning arms against a lower acetabular lip, and abutting an upper positioning arm from the plurality of positioning arms against an upper acetabular lip of the acetabular cavity.

9. The method according to claim 1 further comprising attaching respective optical emitters to the at least one tool, the acetabular calibration guide, and the acetabular reference guide.

10. The method according to claim 1 further comprising creating an incision at the acetabular cavity of the patient and cleaning a bone site of the acetabular cavity of the patient before the positioning of the acetabular calibration guide.

11. A method for implantation of an acetabular prosthesis, the method comprising:
  positioning an acetabular calibration guide at an acetabular cavity of a patient;
  positioning an acetabular reference guide at a bone site of the patient separate from the acetabular cavity;
  aligning a calibration signal and a reference signal, the calibration and reference signals being respectively associated with the acetabular calibration guide and the acetabular reference guide;
  removing the acetabular calibration guide and positioning at least one tool at the acetabular cavity of the patient;
  reaming the acetabular cavity of the patient after removing the acetabular calibration guide; and
  aligning a control signal and the reference signal for identifying a desired orientation of the at least one tool relative to the acetabular cavity, the control signal being associated with the at least one tool;
  the aligning of the calibration signal and the reference signal and the aligning of the control signal and the reference signal each comprising aligning respective optical emitter projections;
  wherein the acetabular calibration guide comprises a positioning base configured to mate with the acetabular cavity of the patient; and
    wherein the positioning base includes a supporting foot configured to abut against an internal surface of the acetabular cavity, and a plurality of positioning arms configured to engage with different points on a periphery of the acetabular cavity.

12. The method according to claim 11 further comprising providing a target screen for the aligning of the calibration signal and the reference signal and the aligning of the control signal and the reference signal.

13. The method according to claim 12 wherein the aligning of the calibration signal and the reference signal and the aligning of the control signal and the reference signal each comprises aligning signals at a same point on the target screen.

14. The method according to claim 11 wherein the aligning of the calibration signal and the reference signal is for identifying a desired orientation of the acetabular calibration guide.

15. The method according to claim 11 further comprising inserting a central positioning arm from the plurality of positioning arms in an acetabular fossa.

16. The method according to claim 11 abutting a lower positioning arm from the plurality of positioning arms against a lower acetabular lip, and abutting an upper positioning arm from the plurality of positioning arms against an upper acetabular lip of the acetabular cavity.

17. The method according to claim 11 further comprising attaching respective optical emitters to the at least one tool, the acetabular calibration guide, and the acetabular reference guide.

18. The method according to claim 11 further comprising creating an incision at the acetabular cavity of the patient and cleaning a bone site of the acetabular cavity of the patient before the positioning of the acetabular calibration guide.

* * * * *